US006964645B1

(12) United States Patent
Smits

(10) Patent No.: US 6,964,645 B1
(45) Date of Patent: Nov. 15, 2005

(54) HALLUX VALGUS BRACE

(75) Inventor: Jan F. A. Smits, Helmond (NL)

(73) Assignee: Camp Scandinavia AB, Helsingborg (SE)

( * ) Notice: Subject to any disclaimer, the term of this patent is extended or adjusted under 35 U.S.C. 154(b) by 0 days.

(21) Appl. No.: 09/787,171

(22) PCT Filed: Sep. 15, 1999

(86) PCT No.: PCT/SE99/01608

§ 371 (c)(1),
(2), (4) Date: Jun. 6, 2001

(87) PCT Pub. No.: WO00/15163

PCT Pub. Date: Mar. 23, 2000

(51) Int. Cl.$^7$ .............................. A61F 5/00; A61F 13/06
(52) U.S. Cl. ........................................ 602/30; 128/894
(58) Field of Search ........................... 602/5, 23, 30–31, 602/60–61, 65–66; 128/882, 893–894; D24/192; 36/94–95; 63/15, 9

(56) References Cited

U.S. PATENT DOCUMENTS

| 1,055,810 A | * | 3/1913 | Scholl | 602/30 |
| 1,784,032 A | * | 12/1930 | Stem | 602/30 |
| 2,099,401 A | * | 11/1937 | Jungmann | 602/30 |
| 2,190,016 A | * | 2/1940 | Day | 128/893 |
| 2,335,665 A | * | 11/1943 | Golemerstien | 128/893 |
| 2,354,770 A | * | 8/1944 | Patterson | 602/30 |
| 2,416,823 A | * | 3/1947 | Day | 128/893 |
| 2,471,997 A | * | 5/1949 | Baltor | 602/30 |
| 2,531,851 A | * | 11/1950 | Kiwad | 602/30 |
| 3,049,120 A | * | 8/1962 | Marcus | 602/30 |
| 3,063,446 A | | 11/1962 | Levitt | |
| 3,429,309 A | * | 2/1969 | Kurth et al. | 602/30 |
| 3,595,225 A | * | 7/1971 | Beeman | 602/21 |
| 3,724,458 A | * | 4/1973 | Piper | 602/79 |
| 4,263,902 A | * | 4/1981 | Dieterich | 602/30 |
| 4,632,103 A | | 12/1986 | Fabricant et al. | |
| 4,637,381 A | * | 1/1987 | Jungmann | 602/30 |
| 5,076,263 A | * | 12/1991 | Funatogawa | 602/30 |
| 5,154,692 A | * | 10/1992 | Lockhart | 602/30 |
| 5,437,616 A | * | 8/1995 | Kasahara | 602/30 |
| 5,730,154 A | * | 3/1998 | DeRidder | 128/880 |
| 6,027,467 A | * | 2/2000 | Nakamura et al. | 602/18 |
| 6,110,136 A | * | 8/2000 | Belkin | 602/22 |

FOREIGN PATENT DOCUMENTS

| CH | 564344 | | 7/1975 |
| DE | 454875 | | 1/1928 |
| JP | 410052472 A | * | 2/1998 |
| JP | 10234759 | | 9/1998 |

* cited by examiner

OTHER PUBLICATIONS

Gunn, Christine, "Bones and Joints—A Guide for Students, 3$^{rd}$ Edition," Churchill Livingstone, p. 69, 1996.*

Primary Examiner—Michael A. Brown
Assistant Examiner—Fenn C. Mathew
(74) Attorney, Agent, or Firm—Ladas & Parry LLP

(57) ABSTRACT

The invention relates to a hallux valgus brace, i.e. a brace designed for treatment of non-rigid hallux valgus. The brace comprises a three point lever means for correcting the position of the big toe. According to the invention the complete brace is designed to be located distally of the metatarsal joint. Preferably, the brace comprises a proximal pad pressing on the first phalanx of the big toe, a distal pad pressing on the distal end of the first phalanx of the big toe, and a lever arm pressing on the ball of the foot. The brace can be used during walking and other activities.

8 Claims, 2 Drawing Sheets

HALLUX VALGUS BRACE

FIELD OF THE INVENTION

The present invention relates to a hallux valgus brace, i.e. a brace designed for treatment of non-rigid hallux valgus. The complete brace is positioned in front of the metatarsal joint and can be used during walking and other activities.

STATE OF THE ART

Hallux valgus is a painful malposition of the big toe, where the big toe turns towards the other toes and a bunion is formed on the protruding joint, i.e. the first metatarsal joint. This deformity has been treated in the past mainly by means of night splints or braces. The brace is mainly used during sleeping or resting. The brace uses three pressure points, two of which are located at the metatarsus. Thus, the prior art brace requires support proximal of the metatarsal joint. The brace bridges the metatarsal joint resulting in that the brace is not suitable for walking because the bending of the joint together with the brace is not comfortable or even impossible.

The present invention solves this problem by positioning the complete brace distally of the metatarsal joint. Thus, all components of the brace are located distally of the metatarsal joint and the brace is not affected by the bending of the joint during walking and other activities. In this way, the brace of the invention may be used for conservative dynamic treatment of non-rigid hallux valgus. In other words, the patient may wear the brace practically at all times resulting in an efficient treatment.

SUMMARY OF THE INVENTION

Thus, the present invention provides a hallux valgus brace comprising a three point lever means for correcting the position of the big toe.

According to the invention the complete brace is designed to be located distally of the metatarsal joint. Preferably, the brace comprises a proximal pad pressing on the medial side on the first phalanx of the big toe, a distal pad pressing on the distal end of the first phalanx, and a lever arm pressing on the ball of the foot.

The invention is defined in claim 1 while preferred embodiments are set forth in the dependent claims.

BRIEF DESCRIPTION OF THE DRAWINGS

The invention will be described in detail below with reference to the accompanying drawings in which.

DETAILED DESCRIPTION OF PREFERRED EMBODIMENTS

Figure 1:
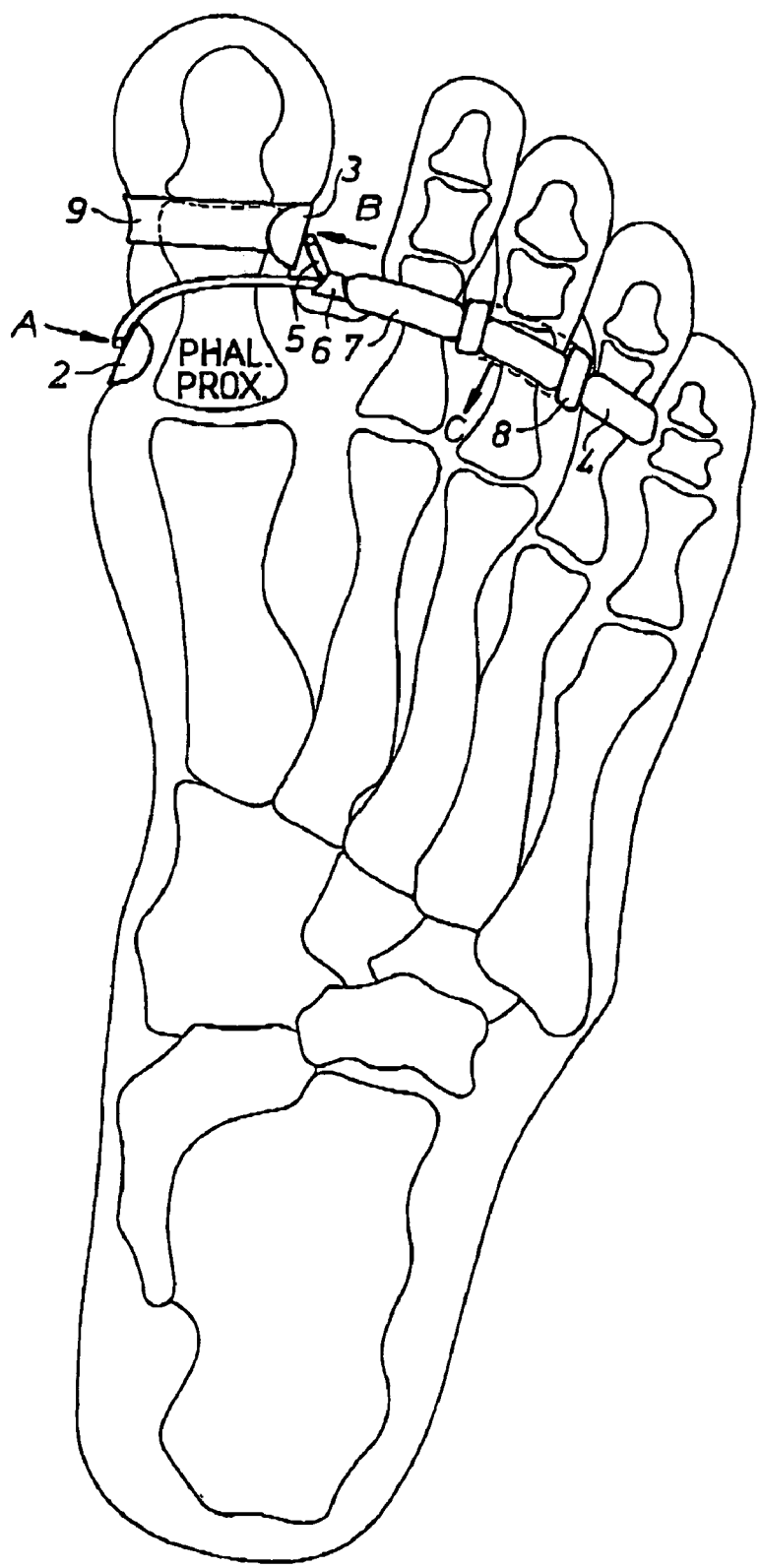
FIG. 1 is a bottom view of the brace on the foot of a patient.
Figure 2:
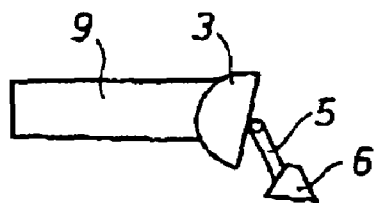
FIG. 2 is a detail view of one component of the brace carrying the distal pad.
Figure 4:
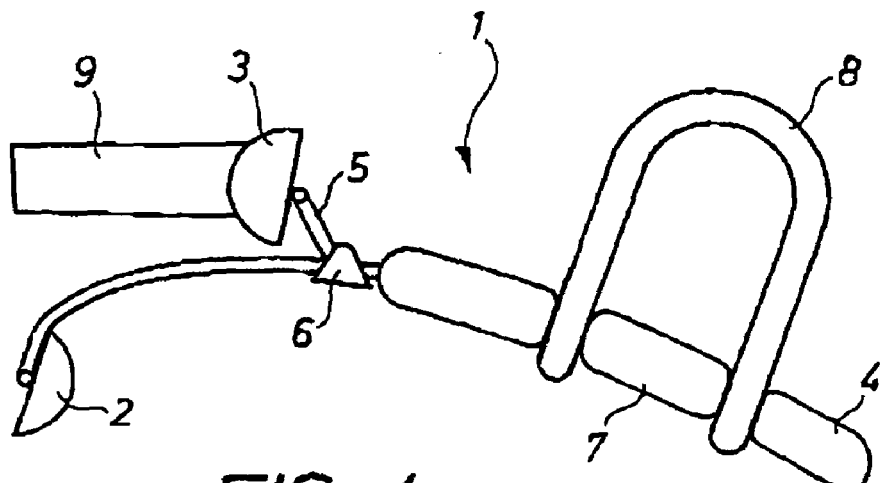
FIG. 4 is a bottom view of the complete brace according to the invention.

The hallux valgus brace according to the invention is now described with reference to the drawings. In FIG. 1, the brace is shown as worn by a patient on a foot. The skeletal bones of the foot are shown for reference. In FIG. 4, the complete brace 1 is shown by itself. The brace is located in the space which exists under the normally slightly bent toes. At the medial side the brace carries a proximal pad 2 pressing on the first phalanx of the big toe. A distal pad 3 is carried by an adjustable arm 5 and presses on the distal end of the big toe, preferably on the distal end of the first phalanx.

The pads 2 and 3 are connected to the frame of the brace by means of hinges, so that the pads can turn and adapt themselves to the curvature of the contact area between the pads and the toe. Thus, the pads 2 and 3 are self-adjusting for better fit and comfort.

Figure 3:
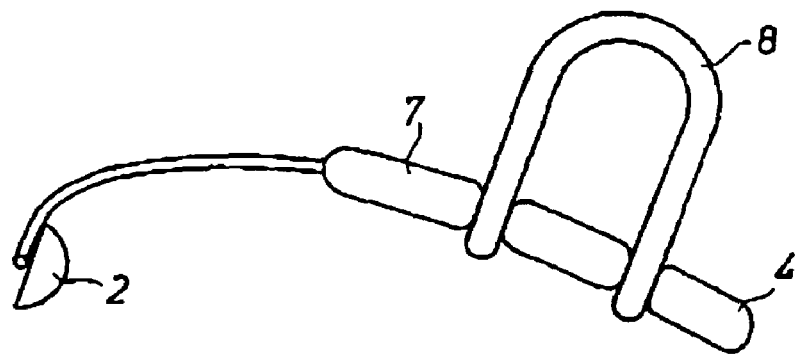
FIG. 3 is a detail view of the main part of the brace.

The lateral part of the brace comprises a lever arm 4 pressing backwards and acting as a counterforce on the ball of the foot. The lever arm 4 also carries a strap 8, best shown in FIGS. 3 and 4. Another toe is inserted through the strap 8 serving to prevent the lever arm 4 from sliding down. This is preferably the third toe since this toe is a little longer and stronger but also e.g. the fourth toe could be used.

The adjustable arm 5 is connected to the main part of the brace by means of a sleeve 6. The sleeve 6 may be-slid to a correct position in order to accommodate various sizes of big toes. When the sleeve 6 is positioned correctly it may be fixed with glue.

The brace is manufactured from stainless steel spring-wire, thickness e.g. 1,75 mm. The pads 2 and 3 are cup shaped pads, made of steel sheet, thickness e.g. 0,6 mm or injection moulded plastic. The adjustable sleeve 6 is also preferably made of stainless steel.

For best comfort the lever arm 4 may carry a silicone tube 7. The strap 8 is suitably made of rubber or plastic, but may also be made of leather, cotton or a hook and loop connection (Velcro® fastening).

The distal pad 3 may carry another strap or fastening means 9 to be located around the big toe and preventing the pad from sliding off. This strap 9 suitably comprises a hook and loop connection for easy fastening and adjustment.

The brace according to the invention can be used in a dynamic way. Since all correcting and stiff parts are located distally of the metatarsal joint the brace does not interfere with normal walking. The brace has a lever means with a clear three point working principle. A force A on the medial side moves the first phalanx laterally while a force B on the lateral side moves the distal end of the first phalanx and the toe medially. The reaction force C is applied against the soft tissue of the ball of the foot.

For the brace of the invention to be efficient the first metatarsal joint needs to be flexible enough to be repositioned and flexed in a horizontal plane. The patient should wear a shoe or slipper providing sufficient room for the medial movement of the toe.

The brace according to the invention is intended to be delivered as an "of the shelf" item and requires adjustments before it can be worn by a patient. Thus, the wire parts of the brace are bent for a proper fit. The sleeve 6 is positioned correctly and preferably glued to secure it to the wire. It is suitable that this work is performed by an orthotist/bandagist or possibly a podiatrist, even if patients eventually may learn to fit the braces themselves.

Thus, the present invention provides several advantages over the prior art. The brace allows for a dynamic treatment since the brace may be used at all times during walking, resting etc. and in normal shoes. The brace is adaptable for various foot sizes by means of some simple adjustments only. The brace is very light-weight and very comfortable.

A person skilled in the art will appreciate that the brace of the invention may be modified without departing from the scope of the invention. Thus, the embodiment shown is just given as an example of shapes and materials that may be used. The scope of the invention is only limited by the claims below.

What is claimed is:

1. A hallux valgus brace comprising a three point lever means for correcting the position of the big toe, wherein the complete brace including the three point lever means is designed to be located distally of the metatarsal joint, the brace comprising a frame, sized and configured to be located substantially under the toes and at a first end providing a first force at a first point on the medial side of the first phalanx of the big toe, at a location between the big toe and the second toe providing a second force at a second point on the lateral side of the distal end of the big toe, and at a second end providing a third force a third point on the ball of the foot;

wherein the brace comprises a proximal pad pressing on the first phalanx of the big toe, a distal pad pressing on the distal end of the big toe, and a lever arm pressing on the ball of the foot;

wherein the distal pad is disposed on an adjustable arm.

2. A brace according to claim 1, wherein the distal pad is adapted to press on the distal end of the first phalanx of the big toe.

3. A brace according to claim 1 or 2, wherein the adjustable arm is secured to a sleeve which is slidable.

4. A brace according to claim 1 or 2, wherein the brace is manufactured from steel wire and steel pads.

5. A brace according to claim 1 or 2, wherein the lever arm is provided with a silicone tube.

6. A brace according to claim 1 or 2, wherein a strap is provided for fitting around the third toe.

7. A brace according to claim 6, wherein the strap is made of rubber or plastic or a hook and loop connection.

8. A brace according to claim 1 or 2, wherein the distal pad carries a strap to be located around the big toe.

* * * * *